United States Patent [19]

Kenney et al.

[11] Patent Number: 4,717,773

[45] Date of Patent: Jan. 5, 1988

[54] SILICATE ESTERS AND ORGANOSILICON COMPOUNDS

[76] Inventors: Malcolm E. Kenney, 1203 Hereford Rd., Cleveland Heights, Ohio 44118; George B. Goodwin, 8031 Greenwood View Dr. #1203, Parma, Ohio 44129

[21] Appl. No.: 784,216

[22] Filed: Oct. 4, 1985

[51] Int. Cl.[4] ............................................. C07F 7/13
[52] U.S. Cl. .................... 556/457; 556/458; 556/482; 556/483; 423/325; 423/326; 423/331; 423/332; 423/334
[58] Field of Search ............... 556/457, 458, 482, 483; 423/325, 326, 331, 332, 334

[56] References Cited

U.S. PATENT DOCUMENTS

| | | | |
|---|---|---|---|
| 2,881,199 | 4/1959 | Bailey et al. | 260/448.8 |
| 3,110,720 | 11/1963 | Pike | 260/448.2 |
| 3,775,457 | 11/1973 | Muraoka et al. | 556/458 X |
| 4,060,537 | 11/1977 | Maass et al. | 260/448.2 E |
| 4,224,234 | 9/1980 | Flick et al. | 556/483 X |
| 4,309,557 | 1/1982 | Compton et al. | 556/453 |

FOREIGN PATENT DOCUMENTS 876645 10/1981 U.S.S.R. .

OTHER PUBLICATIONS

Bleiman and Mercier, "Esterification of Chrysotile-Asbestos by Allyl Alcohol", Inorganic Chemistry, 14 (11), 2853-2854, (1975).

Glasser and Mileson, "Crystal Data for $Na_2Ca_2Si_3O_9$", Journal of the American Ceramic Society, 51, 55, (1968).

Calhoun and Masson, "Trimethylsilyl Derivatives for the Study of Silicate Structures", J. C. S. Dalton, 1282-1291, (1980).

*Primary Examiner*—Paul F. Shaver

[57] ABSTRACT

A method for the preparation of alkoxysilanes and alkoxysiloxanes from a silicate material, and for the further conversion to organosilanes and organosiloxanes. Methods for the preparation of silicate starting materials are also disclosed.

36 Claims, No Drawings

SILICATE ESTERS AND ORGANOSILICON COMPOUNDS

FIELD OF THE INVENTION

This invention relates generally to a process for the preparation of silicate esters and organosilicon compounds, and more particularly to a process for the formation of a variety of alkyl silicates from metal silicates and the synthesis of organosilanes and organosiloxanes from them.

BACKGROUND OF THE INVENTION

The process commonly used commercially for the production of the economically most important monomeric alkoxysilane, tetraethoxysilane, involves two main steps. The first of these entails the synthesis of silicon tetrachloride. This can be made in a variety of ways. In one, silica (sand) is reduced to elemental silicon with carbon in an electric arc furnace, and this is then chlorinated with elemental chlorine. The reduction of the silica to silicon consumes large amounts of electrical energy, a fact reflected in the cost of the silicon. Once the silicon tetrachloride has been prepared, it is reacted with ethanol to produce the tetraethoxysilane:

$$SiCl_4 + 4C_2H_5OH \rightarrow Si(OC_2H_5)_4 + 4HCl$$

An economically important alkoxysiloxane is made by the hydrolysis of tetraethoxysilane. It contains 40 wt % $SiO_2$ and is often called ethyl silicate 40.

Various alkoxysilanes are made by a transesterification process:

$$Si(OR)_4 + 4R'OH \xrightarrow{catalyst} Si(OR')_4 + 4ROH$$

Among the catalysts used for this process are sodium alkoxides. This process is used mainly for the preparation of the alkoxysilanes of alcohols with relatively high boiling points.

The process currently most widely used commercially to make alkyl silicones, and particularly methyl silicones, is over forty years old. It is generally known as the direct process. The first step involves the reduction of silica (sand) to elemental silicon in an electric arc furnace. This step consumes large amounts of electrical energy, a fact reflected in the price of silicon produced by this process. The second step involves the oxidation of silicon with methyl chloride in the presence of a copper catalyst. This step produces $(CH_3)_2SiCl_2$ and a multitude of other products including $CH_3SiCl_3$. In general, this step is conducted so as to maximize the production of $(CH_3)_2SiCl_2$, which is then separated from the other products by distillation. This separation requires careful control of conditions because $(CH_3)_2SiCl_2$ and $CH_3SiCl_3$ have boiling points which differ by only 4° C. and, because, in general, high purity $(CH_3)_2SiCl_2$ is required for the next step in the process. Due account must also be taken of the corrosive and toxic nature of many of the species produced in this step. Once the pure methylchlorosilanes are isolated, they are hydrolyzed to form silicones:

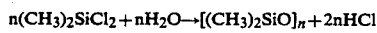
$$n(CH_3)_2SiCl_2 + nH_2O \rightarrow [(CH_3)_2SiO]_n + 2nHCl$$

The resulting mixture is then either separated by distillation or rearranged in the presence of an acid or a base catalyst to give the desired products.

In molecular terms, the direct process involves three steps. The first leads to displacement of all the oxygen atoms on the silicon, the second leads to methylation of the silicon atoms, and the third leads to the attachment of some oxygen atoms on the silicon atoms and to the formation of the desired silicon-oxygen backbone.

Two other processes are also important in the synthesis of silicones. In one, $HSiCl_3$ is produced by the reaction of silicon with HCl or by other means. The $HSiCl_3$ is then catalytically added to olefins:

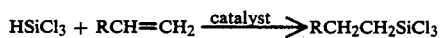
$$HSiCl_3 + RCH=CH_2 \xrightarrow{catalyst} RCH_2CH_2SiCl_3$$

The resulting organochlorosilanes are used directly or are converted into silicones.

In the second of these processes chlorosilanes are treated with organometallic reagents:

$$SiCl_4 + 2RMgX \rightarrow R_2SiCl_2 + 2MgXCl$$

Again the resulting organochlorosilanes, after being separated, are used directly or are converted to silicones.

The latter two processes are used primarily for the production of silicones in which some of the organic groups are other than methyl groups. It is apparent that these two processes and the direct process all have undesirable features.

In other work related to the field of the present invention, Compton and Petraitis (U.S. Pat. No. 4,309,557) describe the preparation of organosiloxanes by the treatment of organoalkoxydisiloxanes and organoalkoxytrisiloxanes with Grignard reagents. This work shows that organosiloxanes can be made from such precursors, and suggests that organosiloxanes can be made from siloxane compounds containing only alkoxy groups. Calhoun and Masson (J.C.S. Dalton 1980, 1282) found that hexaisopropoxycyclotrisiloxane is formed as a very minor byproduct when pseudowollastonite, $Ca_3Si_3O_9$, is treated with trimethylchlorosilane, hexamethyldisiloxane, and isopropyl alcohol. This work shows that alkoxysiloxanes can be made from silicates as byproducts under the reaction conditions used by the authors.

Further, it should be noted that Bleiman and Mercier (Inorg. Chem. 1975, 14, 2853) found that the sheet silicate chrysotile, $Mg_3Si_2O_5(OH)_4$, (common asbestos) can be partially converted to a partially esterified sheet silicate by treating it with hydrochloric acid and isopropyl alcohol and then treating the resulting material with allyl alcohol and pyridine.

SUMMARY OF THE INVENTION

It has been discovered that alkoxysilanes can be prepared by suspending an orthosilicate in an alcohol, treating the suspension with a strong acid such as hydrochloric acid, heating the mixture, removing the low boiling components from the resulting mixture, and then isolating the alkoxysilane (i.e., silicate ester) from the residue. It has also been discovered that alkoxysiloxanes can be prepared by suspending cyclic or acyclic silicates in an alcohol, treating the suspension with a strong acid such as hydrochloric acid, heating the mixture, removing the low boiling components from the resulting mixture, and then isolating the alkoxysiloxane (i.e., silicate ester) from the residue. The starting silicate may be either natural or synthetic. If an alkoxysiloxane is to be made, it is necessary only that the silicon-oxygen backbone which is desired in the alkoxysiloxane be provided in whole or in part in the silicate. It is notable in the process of the invention that when alkoxysiloxanes are to be made, the basic silicon-oxygen backbone is preserved in whole or in part. It is also notable that both when alkoxysilanes and alkoxysiloxanes are to be made, the silicon remains in an oxidized state throughout.

It has further been discovered that alkoxysilanes and alkoxysiloxanes having silicon-oxygen arrangements unlike that of the parent silicates can be made by suspending a silicate in an alcohol, treating the suspension with a strong acid such as hydrochloric acid, heating the mixture, removing the low boiling components from the resulting mixture, and then isolating the alkoxysilane or alkoxysiloxane from the residue.

In a further embodiment of the invention, the alkoxysilanes and alkoxysiloxanes are reacted with an alkylating agent to prepare various organosilanes or organosiloxanes, i.e., silicones.

DETAILED DESCRIPTION OF THE INVENTION

According to the present invention, a wide variety of metal silicates are suitable as starting materials in the preparation of alkoxysilanes from orthosilicates and for the further preparation of organosilanes. Natural and synthetic materials containing the orthosilicate ion $SiO_4^{4-}$ are generally useful, and include beta-$Ca_2SiO_4$, gamma-$Ca_2SiO_4$, $Ca_3SiO_5$, $CaMgSiO_4$ (monticellite), and $Zn_2SiO_4$ (willemite), as well as mixtures such as slags and Portland cement.

Also according to the present invention, a wide variety of metal silicates are suitable as starting materials in the preparation of alkoxysiloxanes having silicon-oxygen backbones in whole or in part like those of the parent metal silicates and for further preparation of organosiloxanes. Natural and synthetic materials containing the linear oligomeric silicate ion $Si_2O_7^{6-}$ are generally useful including $Zn_4Si_2O_7(OH)_2 \cdot H_2O$ (hemimorphite), $Ca_2MgSi_2O_7$ (akermanite), $Ca_3Si_2O_7$ (rankinite), and $Ca_2ZnSi_2O_7$ (hardystonite). It has further been found that cyclic silicates such as $Ca_3Si_3O_9$ (pseudowollastonite), $Ca_3Si_3O_9 \cdot H_2O$ (rosenhahnite), $Ca_2BaSi_3O_9$ (walstromite), alpha-$Sr_3Si_3O_9$, delta-$Sr_3Si_3O_9$, $Ba_3Si_3O_9$, $Mn_3Si_3O_9$ (rhodonite), $M_1$-$Pb_2SiO_4$, $K_4H_4Si_4O_{12}$, $CaAl_2Si_4O_{12} \cdot 4H_2O$ (laumontite), delta'-$Sr_4Si_4O_{12}$, $Ba_5Si_4O_{12}(OH)_2$, $Cu_6Si_6O_{18} \cdot 6H_2O$ (dioptase), $Na_4Ca_4Si_6O_{18}$, and $Ca_7Si_6O_{18}CO_3 \cdot 2H_2O$ (scawtite), which are representative of materials containing the cyclic silicate ions $Si_3O_9^{6-}$, $Si_4O_{12}^{8-}$, and $Si_6O_{18}^{12-}$ are also suitable.

Additional materials believed to be suitable for conversion to alkoxysiloxanes are those which contain the linear oligomeric ions $[Si_3O_{10}]^{8-}$ and $[Si_4O_{13}]^{10-}$, the linear polymeric ion $[SiO_3]_n^{2n-}$, and the cyclic ions $Si_7O_{21}]^{--}$, $[Si_8O_{24}]^{16-}$, $[Si_9O_{27}]^{18-}$, and $[Si_{12}O_{36}]^{24-}$. Representative compounds would include $Na_2Al_2Si_3O_{10} \cdot 2H_2O$ (natrolite), $CaSiO_3$ (wollastonite), and $Ba_7Si_7O_{21} \cdot 10BaCl_2$. Other starting materials are encompassed although not specifically recited.

Further, according to the invention, a wide variety of metal silicates are suitable as starting materials in the preparation of alkoxysilanes and alkoxysiloxanes having silicon-oxygen arrangements unlike those of the parent metal silicates and for the further preparation of organosilanes and organosiloxanes These encompass the materials recited above.

In the method of the invention for the preparation of alkoxysilanes, the starting silicate (i.e., a salt derived from $SiO_2$) provides the silicon upon which the subsequent steps are carried out. For the preparation of alkoxysiloxanes having backbones like those of the parent metal silicates, the starting silicate provides the silicon-oxygen backbone upon which the subsequent steps are carried out. For the preparation of alkoxysilanes and alkoxysiloxanes having different silicon-oxygen arrangements than their parent silicates, the starting silicate provides the silicon upon which subsequent steps are carried out.

Throughout the process in all cases the silicon remains in an oxidized condition.

As a first step, the silicate is treated with an anhydrous or aqueous strong acid in an alcohol solution. Although the silicate may be directly contacted with the acid solution, it is preferred to suspend the silicate as a powder or other finely divided form in an alcohol to facilitate the reaction. All of the $C_{1-8}$ alcohols are satisfactory for this purpose, although methanol, ethanol, n-propanol, isopropanol, n-butanol, and sec-butanol are preferred. The strong acid solution is then advantageously prepared using the same alcohol used for the silicate suspension.

The strong acid used for the step of rendering labile the pendent oxygen atoms on the starting silicate is usually selected from hydrochloric, hydrobromic, sulfuric, phosphoric, and oxalic acids, with hydrochloric acid being preferred for ease of handling. The acid may be anhydrous or aqueous and its concentration in the solution may vary over a wide range, from 0.01 to 18M, and still be useful. However, sufficient acid should be present in the solution containing the silicate to ensure displacement of all or nearly all of the metal ions of the silicate. The temperature of the solution during the initial period of contact between the acid and the silicate should ideally be maintained in a range between about $-30°$ C. and the boiling point of the alcohol. A lower temperature reduces the incidence of undesirable side reactions in the preparation of the alkoxysilanes and in the preparation of the alkoxysiloxanes having silicon-oxygen frameworks based on those of the parent silicate ions, but too low a temperature leads to long reaction times. A temperature between 0° and 25° C. is preferred.

After the acid and the silicate have been thoroughly mixed and the reaction is proceeding, it is necessary to heat the reaction and to remove byproduct water to allow the reaction to go to completion. The water removal can be accomplished by standard techniques such as use of a desiccant or molecular sieves. However, an azeotropic distillation is most efficient. Several of the alcohols which may be used as a reactant form azeotropes with water, and the reaction mixture can be heated to strip off water and other low boiling components without further treatment. Alternatively, an otherwise inert azeotrope former can be added to the reaction mixture prior to distillation. Toluene or chloroform have been found to be well suited for this purpose.

When the heating of the reaction mixture and the removal of the water are complete, it is desirable to separate the reaction products from the byproduct salts. This is most easily accomplished by extraction with an organic solvent. Hexane, heptane, and pentane have been found to be most useful for this purpose, with pentane being the preferred solvent. At this point in the process it may also be useful to filter the organic solvent extract to separate out unreacted and byproduct solids.

The organic solvent extract, containing the desired alkoxysilanes and/or alkoxysiloxanes, is concentrated to isolate the product. This concentration is carried out using conventional methods such as evaporation or distillation.

The products isolated are liquids or solids. When pure they are colorless. They have moderate chemical reactivity. For example, they hydrolyze slowly in the presence of water. They can be used as synthetic intermediates, hydraulic fluids, heat-transfer media, and binders.

In a further embodiment of the invention, the ester products prepared as described are treated to form organosilanes or organosiloxanes, i.e., silicones. The esters are reacted by contacting them with an alkylating agent, such as a Grignard reagent or an organolithium reagent. This reaction is preferably conducted in an ether solution. Diethyl ether, diisopropyl ether, and tetrahydrofuran are representative of useful ethers for this purpose. The reaction is generally conducted at a temperature below about 20° C. to reduce undesirable side reactions, and the organosilane and/or organosiloxane products are then preferably isolated by a combination of extraction and separation steps using organic solvents and aqueous acid solutions.

The products isolated are liquids or solids. When pure they are colorless. When the organic groups are methyl, they are stable chemically. They can be used to make synthetic elastomers and resins, and can also be used as hydraulic fluids, heat-transfer media, and lubricants.

In the method of the invention for the synthesis of $Na_4Ca_4Si_6O_{18}$, sources of silicon, oxygen, sodium, and calcium are heated together at temperatures just below the melting point of $Na_4Ca_4Si_6O_{18}$. Convenient sources of silicon and oxygen are silica ($SiO_2$), wollastonite ($CaSiO_3$), and sodium silicate. Convenient sources of sodium are sodium carbonate and sodium silicate; and convenient sources of calcium are calcium carbonate, calcium oxide, and wollastonite ($CaSiO_3$). Although the mixture of materials may be heated just once, it is preferred to heat it, cool and grind it, and then repeat the cycle several times.

The product isolated is a white solid. It is useful for making alkoxysiloxanes by the process described.

The invention is further illustrated by the following specific examples.

EXAMPLE 1

Preparation of $Na_4Ca_4Si_6O_{18}$. A mixture of $Na_2CO_3$ (20.3 g), $CaCO_3$, and $SiO_2$ (34.6 g) contained in a platinum crucible was heated in a muffle furnace (1080° C.) for 8 h. The resultant was cooled, crushed to a fine powder, and heated (1080° C.) for 8 h. Again the resultant was cooled, crushed, and heated (1080° C.) for 8 h. The product was cooled and crushed (67.4 g, 99%); X-ray diffraction, d(rel intensity) 3.72(33), 3.35(37), 3.31(55), 2.66(100), 2.61(99), 1.87(70) Å.

EXAMPLE 2

Tetraethoxysilane from gamma-Calcium Orthosilicate (gamma-$Ca_2SiO_4$) An HCl-ethanol solution (8.4 M, 31.8 mL) was slowly added (~5 mL/min) to a stirred, cooled (0° C.) suspension of gamma-$Ca_2SiO_4$ (11.0 g) in ethanol (470 mL). The mixture formed was held for 7 min while being kept cool and was filtered. The filtrate was cooled (~0° C.), and, while being kept cool, was slowly added (~10 mL/min) to a solution of ethanol (500 mL) and toluene (1100 mL) which was being distilled at a moderate rate (~16 mL/min). The solution formed was distilled until most of its more volatile components (1825 mL) had been stripped off, and then the remainder was extracted with pentane (400 mL). Vacuum concentration (~50 torr, 40° C.) of the extract followed by vacuum distillation (0.003 torr) of the resulting concentrate yielded a clear, colorless liquid (18.2 g).

Analysis of the product by gas chromatography showed the presence of tetraethoxysilane, hexaethoxydisiloxane, octaethoxytrisiloxane, and other nonsolvent species. The nonsolvent species are thought to be mostly ethoxysiloxanes. Toluene was also found. Tetraethoxysilane constituted most (~71% based on peak integration) of the nonsolvent portion of the chromatographable liquid. Analysis of the liquid by infrared spectroscopy indicated the absence of silanol-containing species.

EXAMPLE 3

Tetraethoxysilane from Portland cement. An HCl-ethanol solution (8.3 M, 60.1 mL) was slowly added (~8 mL/min) to a stirred, cooled (0° C.) suspension of Portland cement (Lone Star Industries, Maryneal Zero $C_3A$ Type III; 18.0 g) in ethanol (440 mL). The mixture formed was held for 9 min while being kept cool and was filtered. The filtrate was cooled (~0° C.), and, while being kept cool, was slowly added (~10 mL/min) to a solution of ethanol (500 mL) and toluene (1100 mL) which was being distilled at a moderate rate (~16 mL/min). The solution formed was distilled until most of its more volatile components (1812 mL) had been stripped off, and then the remainder was extracted with pentane (450 mL). Vacuum concentration (~50 torr, 37° C.) of the extract followed by vacuum distillation (~0.01 torr) of the resulting concentrate yielded a clear, nearly colorless liquid (24.7 g).

Analysis of the liquid by gas chromatography and mass spectrometry showed the presence of tetraethoxysilane, hexaethoxydisiloxane, octaethoxytrisiloxane, octaethoxycyclotetrasiloxane, hexaethoxycyclotrisiloxane, and other nonsolvent species. The nonsolvent species were thought to be mostly ethoxysiloxanes. Toluene was also found. Tetraethoxysilane and hexaethoxydisiloxane constituted most (~75%) of the nonsolvent portion of the chromatographable liquid. Analysis of the product by infrared spectroscopy indicated the absence of silanol-containing species.

EXAMPLE 4

Ethoxysiloxanes from Hemimorphite ($Zn_4Si_2O_7$·$(OH)_2$·$H_2O$). An HCl-ethanol solution (9.9 M, 8.8 mL) was added to a stirred suspension (0° C.) of hemimorphite (well-picked crystals, crushed, 5.0 g) in ethanol (150 mL). Toluene (150 mL) was added to the mixture formed and the resultant was freed by distillation of most (298 mL) of its volatile components. The remainder was extracted with pentane (75 mL), and the extract was decanted and vacuum concentrated (~50 torr, 22° C.). This gave a light yellow oil (6.3 g).

Analysis of the oil by gas chromatography showed the presence of octaethoxycyclotetrasiloxane, hexaethoxydisiloxane, octaethoxytrisiloxane, hexaethoxycyclotrisiloxane, tetraethoxysilane, pentane, toluene, and a series of unidentified species. The unidentified species are thought to be mostly ethoxysiloxanes. The first two ethoxysiloxanes listed made up a substantial portion (~42%) of the nonsolvent, chromatographable fraction of the product, while the first four made up more than half (~56%) of it. Analysis of the product by infrared spectroscopy showed the virtual absence of silanol-containing species.

EXAMPLE 5

Ethoxysiloxanes from Pseudowollastonite ($Ca_3Si_3O_9$). An HCl-ethanol solution (10.1 M, 77.0 mL) was added to a stirred suspension (22° C.) of synthetic pseudowollastonite (prepared by heating wollastonite to 1300° C. for 65 h, powder, 30.0 g) in ethanol (900 mL). The suspension formed was stirred for 80 min at 22° C. Toluene (1.0 L) was added to the resultant and the mixture formed was stripped by distillation of most (1840 mL) of its low boiling components. The residue was extracted with pentane (250 mL). Filtration and vacuum concentration (~50 torr, 62° C.) of the extract yielded a colorless liquid (15.3 g.).

Gas chromatographic analysis of the product revealed the presence of octaethoxytrisiloxane, hexaethoxycyclotrisiloxane, hexaethoxydisiloxane, tetraethoxysilane, octaethoxycyclotetrasiloxane, toluene, and a group of unidentified species. Again the unidentified species are thought to be mostly ethoxysiloxanes. Of the nonsolvent portion of the chromatographable product, the first two ethoxysiloxanes mentioned made up nearly half (~46%) of it, while all five made up about three-quarters (~76%) of it. Infrared analysis of the product showed the presence of silanol-containing species.

EXAMPLE 6

Ethoxysiloxanes from Dioptase ($Cu_6Si_6O_{18}.6H_2O$). An HCl-ethanol solution (9.5 M, 4.3 mL) was added to a stirred suspension (0° C.) of dioptase (well-picked crystals, crushed, 3.0 g) in ethanol (75 mL). Toluene (75 mL) was added to the mixture formed and the resultant was freed of most (132 mL) of its volatile components by distillation. The residue was extracted with pentane (85 mL), and the extract was filtered and vacuum concentrated (~50 torr, 60° C.). This gave a yellow oil (2.5 g).

By gas chromatographic analysis decaethoxybicyclo[5.5.1]hexasiloxane, decaethoxybicyclo[5.3.3]hexasiloxane, octaethoxytricyclo[5.5.1.1$^{3,9}$]hexasiloxane, toluene, and other species, apparently mostly ethoxysiloxanes, were found in the product. The three ethoxysiloxanes identified accounted for nearly all (~93%) of the nonsolvent, chromatographable portion of the product. Infrared analysis indicated the presence of silanol-containing species in the product.

EXAMPLE 7

Ethoxysiloxanes from $Na_4Ca_4Si_6O_{18}$. Over 46 min an HCl-ethanol solution (3.5 M, 300 mL) was added to a stirred suspension (0° C.) of $Na_4Ca_4Si_6O_{18}$ (60.0 g) in ethanol (700 mL). Toluene (1.1 L) was added to the resultant and the mixture formed was stripped by distillation of most (1920 mL) of its low boiling components. The residue was extracted with pentane (350 mL) and filtered. Vacuum concentration (~50 torr, 70° C.) of the filtrate gave a light yellow oil (45.7 g).

Analysis of the oil by gas chromatography and mass spectrometry showed the presence of the following species: decaethoxybicyclo[5.5.1]hexasiloxane MS(70 eV) m/z(rel intensity) 685[(M-OEt)$^+$, 3], 415[(M-OEt-9C$_2$H$_4$-H$_2$O)$^+$, 100], 397[M-OEt-9C$_2$H$_4$-2H$_2$O)$^+$, 25]; decaethoxybicyclo[5.3.3]hexasiloxane MS(70 eV) m/z(rel intensity) 685[(M-OEt)$^+$, 6], 415[(M-OEt-9C$_2$H$_4$-H$_2$O)$^{30}$, 100], 397[(M-OEt-9C$_2$H$_4$-2H$_2$O)$^+$, 26]; hexaethoxydisiloxane MS(70 eV) m/z(rel intensity) 297[(M-OEt)$^+$, 100], 269[(M-OEt-C$_2$H$_4$)$^+$, 16], 157[(M-OEt-5C$_2$H$_4$)$^{30}$, 15]; octaethoxycyclotetrasiloxane MS(70 eV) m/z(rel intensity) 491[(M-OEt)$^{30}$, 28], 417[(M-OEt-2C$_2$H$_4$-H$_2$O)$^+$, 43], 277[(M-OEt-7C$_2$H$_4$-H$_2$O)$^+$, 100]; and octaethoxytricyclo[5.5.1.1$^{3,9}$]hexasiloxane MS(70 eV) m/z(rel intensity) 611[(M-OEt)$^+$, 11], 415[M-OEt-7C$_2$H$_4$)$^+$, 100], 397[(M-OEt-7C$_2$H$_4$H$_2$O)$^+$, 40]. Toluene and other species, presumed to be mostly ethoxysiloxanes, were also found. The first two ethoxysiloxanes listed constituted about two-thirds (~67%) of the nonsolvent portion of the product that was chromatographable. Analysis of the product by infrared spectroscopy showed that it contained species with silanol groups.

EXAMPLE 8

Distilled Ethoxysiloxanes from $Na_4Ca_4Si_6O_{18}$. A sample of the crude ethoxysiloxanes product described in Example 7 (44.3 g) was vacuum distilled (0.01 torr) with a simple column (8.50 g, 19%).

Analysis of the product, a colorless oil, by gas chromatography and mass spectrometry showed the presence of the following species: decaethoxybicyclo[5.5.1]hexasiloxane MS(70 eV) m/z(rel intensity) 685[(M-OEt)$^+$, 5], 415[(M-OEt-9C$_2$H$_4$-H$_2$O)$^+$, 100], 397[(M-OEt-9C$_2$H$_4$-2H$_2$O) 24]; decaethoxybicyclo[5.3.3]hexasiloxane MS(70 eV) m/z(rel intensity) 685[(M-OEt)$^{30}$, 12], 415[(M-OEt-9C$_2$H$_4$-H$_2$O)$^{30}$, 100], 397[(M-OEt-9C$_2$H$_4$-2H$_2$O)$^{30}$, 25]; a decaethoxyheptasiloxane MS(70 eV) m/z(rel intensity) 745[(M-OEt)$^+$, 26], 671[(M-OEt-2C$_2$H$_4$-H$_2$O) 100], 475[(M-OEt-9C$_2$H$_4$-H$_2$O) octaethoxycyclotetrasiloxane MS(70 eV) m/z(rel intensity) 491[(M-OEt)$^+$, 29], 417[(M-OEt-2C$_2$H$_4$-H$_2$O)$^+$, 50], 277[(M-OEt-7C$_2$H$_4$H$_2$O)$^+$, 100]; octaethoxytricyclo[5.5.1.1$^{3,9}$]hexasiloxane MS(70 eV) m/z(rel intensity) 611[(M-OEt)$^+$, 9], 415[M-OEt-7C$_2$H$_4$)$^{30}$, 100], 397[M-OEt-7C$_2$H$_4$-H$_2$O)$^{30}$, 43]; hexaethoxydisiloxane MS(70 eV) m/z(rel intensity) 297[(M-OEt)$^+$, 100], 269[(M-OEt-C$_2$H$_4$)$^{30}$, 18], 157[(M-OEt-5C$_2$H$_4$)$^{30}$, 16]; and octaethoxytrisiloxane MS(70 eV) m/z(rel intensity) 431[(M-OEt)$^+$, 29], 235[(M-OEt-7C$_2$H$_4$)$^+$, 80], 217[(M-OEt-7C$_2$H$_4$-H$_2$O)$^{30}$, 44]. Ethanol and other species, likely mostly additional ethoxysiloxanes, were also found. Most (~70%) of the nonsolvent portion of the chromatographable product was made up of the first two ethoxysiloxanes listed. Infrared spectroscopy showed the product to be virtually free of silanol-containing species.

EXAMPLE 9

Ethoxysiloxanes from $Na_4Ca_4Si_6O_{18}$. An HCl-ethanol solution (9.1 M, 29.5 mL) was slowly added (~6 mL/min) to a stirred, cooled (0° C.) suspension of $Na_4Ca_4Si_6O_{18}$ (15.0 g) in ethanol (460 mL). The mixture formed was held for 40 min while being kept cool and was filtered. The filtrate was cooled (~0° C.), and, while being kept cool, was slowly added (~10 mL/min) to a solution of ethanol (500 mL) and toluene (1100 mL) that was being distilled at a moderate rate (~16 mL/min). The solution formed was distilled until most of its volatile components (1867 mL) had been stripped off, and then the remainder was extracted with pentane (350 mL). The extract was vacuum concentrated and the concentrate was slowly added (~0.3 mL/min) to a solution of ethanol (175 mL) and toluene (175 mL) that was being distilled at a moderate rate (overall average 0.9 mL/min). The solution formed was distilled until most of its more volatile components (339 mL) had been stripped off. Vacuum concentration (~50 torr, 55° C.) of the residue and vacuum distillation of the resulting concentrate yielded a clear, colorless liquid (14.2 g).

Analysis of the liquid by gas chromatography showed the presence of decaethoxybicyclo[5.5.1]hexasiloxane, decaethoxybicyclo[5.3.3]hexasiloxane, tetraethoxysilane, hexaethoxydisiloxane, octaethoxytricyclohexa[5.5.1.1$^{3,9}$-siloxane, and other nonsolvent species. From other work it is concluded that one of these species is dodecaethoxycyclohexasiloxane. Toluene was also found. The two bicyclohexasiloxanes constituted much (~53%) of the nonsolvent portion of the chromatographable liquid. Analysis of the liquid by infrared spectroscopy indicated the presence of very small amounts of silanol-containing species.

EXAMPLE 10

Propoxysiloxanes from Pseudowollastonite ($Ca_3Si_3O_9$). An HCl-n-propanol solution (7.0 M, 38.5 mL) was added to a stirred suspension (0° C.) of pseudowollastonite (prepared by heating wollastonite to 1300° C. for 65 h, powder, 10.0 g) in n-propanol (300 mL). Toluene (400 mL) was added to the resultant. The mixture formed was stripped by distillation of most (660 mL) of its low boiling components, further stripped under vacuum of more of its low boiling components, and the residue was extracted with pentane (135 mL). Filtration and vacuum concentration (~50 torr, 65° C.) of the extract gave a light yellow oil (8.3 g).

Analysis of the oil by gas chromatography showed the presence of octapropoxytrisiloxane, hexapropoxycyclotrisiloxane, tetrapropoxysilane, hexapropoxydisiloxane, toluene, and unidentified species, presumably mostly propoxysiloxanes. The first two propoxysiloxanes listed comprised most (~17%) of the nonsolvent portion of the chromatographable product, while all four comprised nearly all (~90%) of it. Infrared spectroscopy showed that the product contained species with silanol groups.

EXAMPLE 11

Ethoxysiloxanes from gamma-Calcium Orthosilicate (gamma-$Ca_2SiO_4$) Over a 5 min interval, an HCl-ethanol solution (10.7 M, 120 mL) was added to a stirred suspension (0° C.) of synthetic gamma-$Ca_2SiO_4$ (powder, 50.0 g) in ethanol (880 mL). Toluene (1.05 L) was added to the mixture formed and the resultant was freed of most (1950 mL) of its volatile components by distillation. The residue was extracted with pentane (350 mL) and the extract was filtered. Vacuum concentration of the filtrate (~50 torr, 80° C.) gave a yellow oil (33.2 g).

Analysis of the oil by gas chromatography showed the presence of octaethoxycyclotetrasilokane, octaethoxytrisiloxane, hexaethoxydisiloxane, tetraethoxysilane, hexaethoxycyclotrisiloxane, toluene, and a group of unidentified species. These latter species were presumed to be mostly ethoxysiloxanes. The octaethoxycyclotetrasiloxane accounted for a significant part (~31%) of the nonsolvent fraction of the chromatographable product, while it and the next two ethoxysiloxanes listed accounted for nearly half (~47%) of this fraction. Analysis of the product by infrared spectroscopy indicated the presence of silanol-containing species.

EXAMPLE 12

Methylsiloxanes from gamma-$Ca_2SiO_4$. Over an interval of 37 min, a solution of the Grignard reagent $CH_3MgCl$ in tetrahydrofuran (3.3 M, 177 mL) was added to a stirred (magnetic), cooled (dry ice-acetone) solution of the ethoxysiloxanes produced in Example 11 (19.6 g) in tetrahydrofuran (180 mL). The suspension obtained was stirred for 35 h while being held at low temperature (0° C.), and the mixture formed was concentrated to a semisolid under vacuum (~1 torr, <23° C.). This semisolid was added to a mixture of pentane (500 mL) and aqueous HCl (3.0 M, 390 mL). The organic-siloxane portion of the resulting mixture was isolated by a combination of extraction and separation steps (pentane, 3.0 M HCl). The solution obtained was dried ($CaSO_4$) and filtered. Concentration of the filtrate under vacuum (~50 torr, 30° C.) yielded a light yellow oil (7.8 g).

Analysis of the oil by gas chromatography and mass spectrometry showed the presence of octamethylcyclotetrasiloxane, hexamethyldisiloxane, octamethyltrisiloxane, decamethyltetrasiloxane, decamethylcyclopentasiloxane, decamethylbicyclo[5.5.1]hexasiloxane, decamethylbicyclo [5.3.3]hexasiloxane, tetrahydrofuran, toluene, and other species, presumably mostly methylsiloxanes. The first four methylsiloxanes comprised a significant fraction (~52%) of the nonsolvent portion of the chromatographable product.

EXAMPLE 13

Methylsiloxanes from $Na_4Ca_4Si_6O_{18}$. A solution of the methyl Grignard reagent CH MgCl in tetrahydrofuran (3.3 M, 431 mL) was added over 1 h to a stirred (magnetic), cooled (dry ice-acetone) solution of the ethoxysiloxanes prepared as described in Example 7 (55.3 g) in tetrahydrofuran (450 mL). The resulting suspension, while being held at low temperature (2° C.), was stirred for 2.5 d. The mixture formed was concentrated under vacuum (~1 torr, <23° C.) to a semisolid. This was added to a mixture of pentane (750 mL) and dilute HCl (3.0 M, 600 mL), and the organic-siloxane phase of the resultant was isolated with a sequence of extraction and separation steps (pentane, 2.4 M HCl, water). After being dried ($CaSO_4$), the organic-siloxane phase was filtered and concentrated under vacuum (~50 torr, 75° C.). This gave a light yellow oil (21.1 g).

Analysis of the oil by gas chromatography and mass spectrometry showed the presence of the following species: decamethylbicyclo[5.5.1]hexasiloxane MS(70 eV) m/z(rel intensity) 415[(M-Me)$^+$, 83], 327[(M-Me-SiMe$_4$)$^+$, 100], 73[(SiMe$_3$)$^+$, 78]; decamethylbicyclo[5.3.3]hexasiloxane MS(70 eV) m/z(rel intensity) 415[(M-Me)$^{30}$, 81], 327[(M-Me-SiMe$_4$)$^+$, 100], 73[(SiMe$_3$)$^{30}$, 76]; a tetramethyldisiloxanediol MS(70 eV) m/z(rel intensity) 149[(M-OH)$^+$, 100], 133[(M-OH-CH$_4$)$^+$, 96], 75[(HOSiMe$_2$)$^+$, 28]; octamethyltrisiloxane MS(70 eV) m/z(rel intensity) 221[(M-Me)$^+$, 92], 133[(M-Me-SiMe$_4$)$^+$, 9], 73[(SiMe$_3$)$^+$, 100 ]; decamethyltetrasiloxane MS(70 eV) m/z(rel intensity) 295[(M-Me)$^+$, 29], 207[(M-Me-SiMe$_4$)$^{30}$, 100], 73[(SiMe$_3$)$^{30}$, 89]; octamethylcyclotetrasiloxane MS(70 eV) m/z(rel intensity) 281[(M-Me)+, 100], 73[(SiMe$_3$)+, 9]; decamethylcyclopentasiloxane MS(70 eV) m/z(rel intensity) 355[(M-Me)+, 97], 267[(M-Me-SiMe$_4$)+, 90], 73[(SiMe$_3$)+, 100]; hexamethyldisiloxane MS(70 eV) m/z(rel intensity) 147[(M-Me)+, 100], 131[(M-Me-CH$_4$)+, 7], 73[(SiMe$_3$)+, 20]; a hexamethyltrisiloxanediol MS(70 eV) m/z(rel intensity) 223[(M-OH)+, 27], 207[(M-OH-CH$_4$)+, 100], 75[(HOSiMe$_2$)+, 13]; dodecamethylpentasiloxane MS(70 eV) m/z(rel intensity) 369[(M-Me)+, 24], 281[(M-Me-SiMe$_4$)+1, 100], 147[(Si$_2$OMe$_5$)+, 60], 73[(SiMe$_3$)+, 84]; octamethyltricyclo[5.5.1.1$^{3,9}$]hexasiloxane MS(70 eV) m/z(rel intensity) 401[(M-Me)+, 100], 193[(M-2Me)++, 28]; and tetradecamethylhexasiloxane MS(70 eV) m/z(rel intensity) 443[(M-Me)+, 9], 221[(Si$_3$O$_2$Me$_7$)+, 40], 147[(Si$_2$OMe$_5$)+, 38], 73[(SiMe$_3$)+, 100]. Also found were tetrahydrofuran, toluene, and unidentified species, probably mostly methylsiloxanes. Of the nonsolvent portion of the chromatographable product, the first two species listed constituted a significant fraction ($\sim$20%).

EXAMPLE 14

Methylsiloxanes from Na$_4$Ca$_4$Si$_6$O$_{18}$ via Distilled Ethoxysiloxanes. Over a 1.5 h period, a solution of the methyl Grignard reagent CH$_3$MgCl in tetrahydrofuran (2.8 M, mL) was added to a stirred (magnetic), cooled (dry ice-acetone) solution of the ethoxysiloxanes prepared as described in Example 8 (9.44 g) in tetrahydrofuran (75 mL). The suspension obtained was stirred for 38 h while being held at low temperature (0° C.). Under vacuum ($\sim$1 torr, 23° C.) the mixture formed was concentrated to a semisolid. This was added to a mixture of pentane (250 mL) and aqueous HCl (2.1 M, 303 mL). The organic-siloxane part of the resulting mixture was isolated by a combination of extraction and separation steps (pentane). The solution obtained was dried over CaSO$_4$ and the spent CaSO$_4$ was washed with pentane (75 mL). Filtration and vacuum concentration ($\sim$50 torr, 40° C.) of the solution and washings yielded a light yellow oil (4.40 g). This was vacuum distilled (20 torr). Five roughly equal fractions were collected.

Analysis of the second fraction by gas chromatography and mass spectrometry showed the presence of the following species: decamethylbicyclo[5.5.1]hexasiloxane MS(70 eV) m/z(rel intensity) 415[(M-Me)+, 100], 327[(M-Me-SiMe$_4$)+, 85], 73[(SiMe$_3$)+, 100]; a tetramethyldisiloxanediol MS(70 eV) m/z(rel intensity) 149[(M-OH)+, 98], 133[(M-OH-CH$_4$)+, 100], 75[(HOSiMe$_2$)+, 26]; decamethylbicyclo[5.3.3]hexasiloxane MS(70 eV) m/z(rel intensity) 415[(M-Me)+, 100], 327[(M-Me-SiMe$_4$)+, 82 ], 73[(SiMe$_3$)+, 62]; a hexamethyltrisiloxanediol MS(70 eV) m/z(rel intensity) 223[(M-OH)+, 23], 207[(M-OH-CH$_4$)+, 100], 75[HOSiMe$_2$)+, 12]; octamethyltrisiloxane MS(70 eV) m/z(rel intensity) 221[(M-Me)+, 75], 103[M-2Me)++, 13], 73[(SiM$_3$)+, 100]; octamethylcyclotetrasiloxane MS(70 eV) m/z(rel intensity) 281[(M-Me)+, 100], 73[(SiMe$_3$)+, 8]; decamethylcyclopentasiloxane MS(70 eV) m/z(rel intensity) 355[(M-Me)+, 100], 267[(M-Me-SiMe$_4$)+, 68], 73[(SiMe$_3$)$^{30}$, 91]; decamethyltetrasiloxane MS(70 eV) m/z(rel intensity) 295[(M-Me)+, 42], 207[M-Me-SiMe$_4$)+, 100], 73[SiMe$_3$)$^{30}$, 71]; and dodecamethylpentasiloxane MS(70 eV) m/z(rel intensity) 369[(M-Me)+, 38], 281[(M-Me-SiMe$_4$)+, 100], 73[(SiMe$_3$)+, 55]A group of additional species, probably mostly methylsiloxanes, was also present. A substantial fraction ($\sim$33%) of the nonsolvent, chromatographable portion of the product was made up of the two decamethylbicyclohexasiloxanes.

What is claimed is:

1. A method for preparing alkoxysilanes and alkoxysiloxanes which comprises treating a metal silicate with a solution of anhydrous or aqueous acid in an alcohol, heating the resulting mixture and removing low boiling components from said mixture, then isolating the product from the residue.

2. The method of claim 1 wherein the silicate is a metal salt of silicon dioxide.

3. The method of claim 1 wherein the silicate is a salt containing the orthosilicate ion.

4. The method of claim 3 wherein the silicate is selected from the group consisting of beta-Ca$_2$SiO$_4$, gamma-Ca$_2$SiO$_4$, Ca$_3$SiO$_5$, CaMgSiO$_4$ and Zn$_2$SiO$_4$, or mixtures thereof.

5. The method of claim 1 wherein the silicate is a linear oligomeric silicate.

6. The method of claim 5 wherein the silicate is selected from the group consisting of Zn$_4$Si$_2$O$_7$(OH)$_2$.2-H$_2$O, Ca$_2$MgSi$_2$O$_7$ and Ca$_3$Si$_2$O$_7$, or mixtures thereof.

7. The method of claim 1 wherein the silicate is a linear polymeric silicate.

8. The method of claim 7 wherein the silicate is selected from the group consisting of CaSiO$_3$, BaSiO$_3$ or mixtures thereof.

9. The method of claim 1 wherein the silicate is a cyclic silicate.

10. The method of claim 9 wherein the silicate is selected from the group consisting of Ca$_3$Si$_3$O$_9$, M1(Pb$_2$g)(Si$_4$O$_{12}$) Cu$_6$Si$_6$O$_{18}$.6H$_2$O and Na$_4$Ca$_4$Si$_6$O$_{18}$, or mixtures thereof.

11. The method of claim 9 wherein the cyclic silicate contains the ion [Si$_6$O$_{18}$]$^{12-}$ and is prepared by the steps of:

(a) mixing sources of Na$^{1+}$, Ca$^{2+}$, Si$^{4+}$ and O$^{2+}$; and (b) calcining the resulting mixture at a temperature of at least about 1000° C. until [Si$_6$O$_{18}$]$^{12-}$ is formed.

12. The method of claim 1 wherein the alcohol contains 1–8 carbon atoms.

13. The method of claim 12 wherein the alcohol is selected from the group consisting of methanol, ethanol, n-propanol, isopropanol, n-butanol and sec-butanol, or mixtures thereof.

14. The method of claim 1 wherein the mixture of silicate with acid in alcohol solution is heated and by-product water is removed as a distillate component, the product is extracted from the distillation residue using an organic solvent, and the product is then isolated by distillation of the solvent.

15. The method of claim 1 wherein the mixture of silicate with acid in alcohol solution is added to a distilling alcohol and byproduct water is removed as a distillate component, the product is extracted from the distillation residue using an organic solvent, and the product is then isolated by distillation of the solvent.

16. The method of claim 1 wherein the acid is a strong acid.

17. The method of claim 1 wherein the acid is selected from the group consisting of hydrochloric, hydrobromic, sulfuric, phosphoric, and oxalic acids, or mixtures thereof.

18. The method of claim 1 wherein the acid is hydrochloric acid.

19. The method of claim 1 wherein organosilanes and organosiloxanes are prepared by the additional steps of reacting the product alkoxysilanes and alkoxysiloxanes with an alkylating agent and recovering organosilanes and organosiloxanes.

20. The method of claim 19 wherein the alkylating agent is selected from the group consisting of Grignard reagents and organolithium reagents.

21. The method of claim 19 wherein the organosilanes and organosiloxanes are recovered by extraction and separation steps using pentane and aqueous hydrochloric acid.

22. A method for preparing alkoxysilanes and alkoxysiloxanes which comprises the steps of:
(a) suspending a finely divided silicate in a $C_{1-8}$ alcohol;
(b) contacting the suspension of (a) with a solution of anhydrous or aqueous hydrochloric acid in a $C_{1-8}$ alcohol while maintaining the temperature below about 25° C.;
(c) introducing the mixture formed in (b) slowly into distilling alcohol and simultaneously stripping out low boiling components and byproduct water by distillation;
(d) extracting the residue after distillation with an organic solvent; and
(e) concentrating the solvent extract of (d) to isolate product.

23. The method of claim 22 wherein the alcohol of (a) and (b) is ethanol.

24. The method of claim 22 wherein the amount of hydrochloric acid used in (b) is sufficient to displace all or nearly all of the metal ions of the silicate.

25. The method of claim 22 wherein toluene is added to (c) and byproduct water is removed by azeotropic distillation.

26. The method of claim 22 wherein the organic solvent of (d) is pentane.

27. The method of claim 22 wherein the concentration step (e) is distillation.

28. The method of claim 22 wherein organosilanes and organosiloxanes are prepared by including the additional steps of:
(f) preparing a solution of the product alkoxysilanes and alkoxysiloxanes from (e) in an ether;
(g) adding to the solution of (f) a mixture of alkylating agent in an ether;
(h) maintaining the resulting reaction mixture at a temperature up to the boiling point of the ether until organosilanes and organosiloxanes are formed; and
(i) concentrating the mixture and recovering the organosilanes and organosiloxanes.

29. The method of claim 28 wherein the ether of (f) and (g) is tetrahydrofuran.

30. The method of claim 28 wherein the alkylating agent is a Grignard reagent.

31. The method of claim 28 wherein the organosilanes and organosiloxanes are recovered by extraction and separation steps using pentane and aqueous hydrochloric acid.

32. A method for preparing the cyclic silicate ion $[Si_6O_{18}]^{12-}$ which comprises mixing silica and compounds selected from the alkali metal carbonates and the alkaline earth metal carbonates, or mixtures thereof, and calcining the resulting mixture at a temperature of at least about 1000° C. until $[Si_6O_{18}]^{12-}$ is formed.

33. The compound dodecaethoxycyclohexasiloxane.

34. The compound decaethoxybicyclo[5.5.1]-hexasiloxane.

35. The compound decaethoxybicyclo[5.3.3]-hexasiloxane.

36. The compound octaethoxytricyclo[5.5.1.1$^{3,9}$]-hexasiloxane.

* * * * *

UNITED STATES PATENT AND TRADEMARK OFFICE
CERTIFICATE OF CORRECTION

PATENT NO. : 4,717,773

DATED : January 5, 1988

Page 1 of 3

INVENTOR(S) : Malcolm E. Kenney and George B. Goodwin

It is certified that error appears in the above-identified patent and that said Letters Patent is hereby corrected as shown below:

Column 3, line 61, "$Si_7O_{21}]$" should read --- $Si_7O_{21}]^{14-}$ ---.

Column 4, line 3, "organosiloxanes These" should read --- organosiloxanes. These ---.

Column 5, line 56, "$CaCO_3$" should read --- $CaCO_3$ (38.4 g) ---.

Column 7, line 38, "$(Cu_6Si_6O_{18} \cdot 6H_2O.$" should read --- $(Cu_6Si_6O_{18} \cdot 6H_2O)$. ---.

Column 8, line 8, "$-H_2O)^{30}$" should read --- $-H_2O)^+$ ---.

Column 8, line 8, "$-5C_2H_4)^{30}$" should read --- $-5C_2H_4)^+$ ---.

Column 8, line 12, "$-OEt)^{30}$" should read --- $-OEt)^+$ ---.

Column 8, line 17, "$7C_2H_4H_2O)^+$" should read --- $-7C_2H_4-H_2O)^+$ ---.

Column 8, line 35, "$-2H_2O)$" should read $-2H_2O)^+$, ---.

Column 8, line 36, "$-OEt)^{30}$" should read --- $-OEt)^+$ ---.

Column 8, line 37, "$-H_2O)^{30}$" should read --- $-H_2O)^+$ ---.

Column 8, line 38, "$-2H_2O)^{30}$" should read --- $-2H_2O)^+$ ---.

Column 8, line 40, "$2C_2H_4-H_2O)$" should read --- $2C_2H_4-H_2O)^+$, ---.

Column 8, line 40, "$-9C_2H_4-H_2O)$" should read --- $-9C_2H_4-H_2O)^+$, 22]; ---.

UNITED STATES PATENT AND TRADEMARK OFFICE
CERTIFICATE OF CORRECTION

PATENT NO. : 4,717,773

DATED : January 5, 1988

INVENTOR(S) : Malcolm E. Kenney and George B. Goodwin

It is certified that error appears in the above-identified patent and that said Letters Patent is hereby corrected as shown below:

Column 8, line 43, "$-7C_2H_4H_2O)^+$" should read --- $-7C_2H_4-H_2O)^+$ ---.

Column 8, line 45, "$-7C_2H_4)^{30}$" should read --- $-7C_2H_4)^+$ ---.

Column 8, line 46, "$-H_2O)^{30}$" should read --- $-H_2O)^+$ ---.

Column 8, line 48, "$-C_2H_4)^{30}$" should read --- $-C_2H_4)^+$ ---.

Column 8, line 48, "$-5C_2H_4)^{30}$" should read --- $-5C_2H_4)^+$ ---.

Column 8, line 51, "$-H_2O)^{30}$" should read --- $-H_2O)^+$ ---.

Column 9, line 18, "$[5.5.1.1^{3,9}$" should read --- $[5.5.1.1.^{3,9}]$ ---.

Column 9, line 64, "octaethoxycyclotetrasilokane" should read --- octaethoxycyclotetrasiloxane ---.

Column 10, line 32, "decamethylbicyclo [5.3.3]hexasiloxane" should read --- decamethylbicyclo[5.3.3]hexasiloxane ---.

Column 10, line 40, "CH MgCl" should read --- $CH_3MgCl$ ---.

Column 10, line 61, "$-Me)^{30}$" should read --- $-Me)^+$ ---.

Column 10, line 62, "$(SiMe_3)^{30}$" should read --- $(SiMe_3)^+$ ---.

Column 10, line 68, "$-SiMe_4)^{30}$" should read --- $SiMe_4)^+$ ---.

Column 10, line 68, "$(SiMe_3)^{30}$" should read --- $(SiMe_3)^+$ ---.

UNITED STATES PATENT AND TRADEMARK OFFICE
CERTIFICATE OF CORRECTION

PATENT NO. : 4,717,773
DATED : January 5, 1988
INVENTOR(S) : Malcolm E. Kenney and George B. Goodwin It is certified that error appears in the above-identified patent and that said Letters Patent is hereby corrected as shown below:

Column 11, line 11, "$(SiMe_4)^{+1}$" should read --- $(SiMe_4)^+$ ---.

Column 11, line 27, "(2.8 M, mL)" should read --- (2.8 M, 97 mL) ---.

Column 11, line 62, "$(SiMe_3)^{30}$" should read --- $(SiMe_3)^+$ ---.

Column 11, line 64, "$207[M-Me-SiMe_4)^+$" should read --- $207[(M-Me-SiMe_4)^+$ ---.

Column 11, line 64, "$SiMe_3)^{30}$" should read --- $(SiMe_3)^+$ ---.

Column 11, line 67, "55]A" should read --- 55]. A ---.

Claim 10, Column 12, line 33, "$M1(Pb_2g)(Si_4O_{12})$" should read --- $(Pb_2O)_4(Si_4O_{12})$ ---.

Claim 11, Column 12, line 38, "$O^{2+}$" should read --- $O^{2-}$ ---.

Signed and Sealed this

Twenty-fifth Day of April, 1989

*Attest:*

DONALD J. QUIGG

*Attesting Officer*   *Commissioner of Patents and Trademarks*